(12) United States Patent
Blackwell, Jr. et al.

(10) Patent No.: US 10,658,075 B1
(45) Date of Patent: May 19, 2020

(54) RAPID REPORTING OF MEANINGFUL USE IN ELECTRONIC HEALTH RECORDS

(71) Applicant: ALLSCRIPTS SOFTWARE, LLC, Chicago, IL (US)

(72) Inventors: Gordon Lyles Blackwell, Jr., Raleigh, NC (US); Brent Arasimowicz, Auburn, NH (US); Timothy Early Riely, Raleigh, NC (US)

(73) Assignee: ALLSCRIPTS SOFTWARE, LLC, Chicago, IL (US)

( * ) Notice: Subject to any disclaimer, the term of this patent is extended or adjusted under 35 U.S.C. 154(b) by 1200 days.

(21) Appl. No.: 14/043,420

(22) Filed: Oct. 1, 2013

Related U.S. Application Data (60) Provisional application No. 61/868,516, filed on Aug. 21, 2013.

(51) Int. Cl.
*G06Q 50/00* (2012.01)
*G06F 15/16* (2006.01)
*G16H 10/60* (2018.01)

(52) U.S. Cl.
CPC .................................. *G16H 10/60* (2018.01)

(58) Field of Classification Search
CPC ........ G06Q 50/22; G06Q 50/24; G06Q 10/10; G06Q 10/06; G06Q 10/00; G06Q 10/06311; G06Q 10/0633; G16H 50/20; G16H 50/70; G16H 10/60; G06F 16/2282; G06F 16/23; G06F 16/2365; G06F 16/00
See application file for complete search history.

(56) References Cited

U.S. PATENT DOCUMENTS

| | | | | |
|---|---|---|---|---|
| 2007/0106754 A1* | 5/2007 | Moore | ................ | G06F 17/3089 709/217 |
| 2008/0082359 A1* | 4/2008 | Jung | ....................... | G06F 19/18 705/2 |

* cited by examiner

*Primary Examiner* — Maroun P Kanaan
(74) *Attorney, Agent, or Firm* — Loza & Loza, LLP; Peter Zura (57) ABSTRACT

A system includes a non-transitory computer-readable medium containing computer-executable instructions for providing a method related to rapid reporting of meaningful use in electronic health records. The method includes storing patient encounter data in a database, pre-calculating data related to at least one meaningful use measure, storing the pre-calculated data in a plurality of small staging tables, and compiling the pre-calculated and stored data from the small staging tables into a single table that is adapted to be accessed by reporting software.

10 Claims, 7 Drawing Sheets

| MU_MeasureCore9: Capture Smoking Status (Patient Age > 13) | | | | | | | | | | | | | |
|---|---|---|---|---|---|---|---|---|---|---|---|---|---|
| ProviderID | PatientID | DOS | EncounterID | Den10 | Den11 | Den12 | ... | DenX | Num10 | Num11 | Num12 | ... | NumX |
| Xyz | 1234 | 4/30/2012 | 3445 | 1 | 1 | 1 | ... | 1 | 1 | 1 | 0 | ... | 0 |
| Xyz | 1234 | 4/30/2012 | 3445 | 1 | 1 | 1 | ... | 1 | 1 | 1 | 0 | ... | 0 |
| Xyz | 1234 | 5/30/2012 | 3456 | 0 | 1 | 0 | ... | 0 | 0 | 0 | 0 | ... | 0 |
| Xyz | 5678 | 6/30/2012 | 9383 | 1 | 1 | 1 | ... | 1 | 1 | 1 | 0 | ... | 0 |
| Xyz | 1234 | 7/2/2012 | 23412 | 1 | 1 | 1 | ... | 1 | 1 | 1 | 0 | ... | 0 |

| MU_MeasureCore9: Capture Smoking Status (Patient Age > 13) | | | | | | | | | | | | |
|---|---|---|---|---|---|---|---|---|---|---|---|---|
| ProviderID | PatientID | DOS | EncounterID | Den10 | Den11 | Den12 | ... | DenX | Num10 | Num11 | Num12 | ... | NumX |
| Xyz | 1234 | 4/30/2012 | 3445 | 1 | 1 | 1 | ... | 1 | 1 | 1 | 0 | ... | 0 |
| Xyz | 1234 | 4/30/2012 | 3445 | 1 | 1 | 1 | ... | 1 | 1 | 1 | 0 | ... | 0 |
| Xyz | 1234 | 5/30/2012 | 3456 | 0 | 1 | 0 | ... | 0 | 0 | 0 | 0 | ... | 0 |
| Xyz | 5678 | 6/30/2012 | 9383 | 1 | 1 | 1 | ... | 1 | 1 | 1 | 0 | ... | 0 |
| Xyz | 1234 | 7/2/2012 | 23412 | 1 | 1 | 1 | ... | 1 | 1 | 1 | 0 | ... | 0 |

FIG. 1

| MU_MeasureCore8: Capture Vitals (Patient Age > 2) | | | | | | | | | | | | | | |
|---|---|---|---|---|---|---|---|---|---|---|---|---|---|---|
| ProviderID | PatientID | DOS | EncounterID | Den10 | Den11 | Den12 | ... | DenX | Num10H | Num11W | Num12S | Num13D | NumX |
| Xyz | 1234 | 4/30/2012 | 3445 | 1 | 1 | 1 | ... | 1 | 1 | 1 | 0 | ... | 0 |
| Xyz | 1234 | 4/30/2012 | 3445 | 1 | 1 | 1 | ... | 1 | 1 | 1 | 0 | ... | 0 |
| Xyz | 1234 | 5/30/2012 | 3456 | 0 | 1 | 0 | ... | 0 | 0 | 0 | 0 | ... | 0 |
| Xyz | 5678 | 6/30/2012 | 9383 | 1 | 1 | 1 | ... | 0 | 1 | 1 | 0 | ... | 0 |
| Xyz | 1234 | 7/2/2012 | 23412 | 1 | 1 | 1 | ... | 1 | 1 | 1 | 0 | ... | 0 |

FIG. 2

| MU_MeasureCore4: Transmit Permissible Medication | | | | | | | | | | | | | |
|---|---|---|---|---|---|---|---|---|---|---|---|---|---|
| ProviderID | PatientID | DOS | EncounterID | Den10 | Den11 | Den12 | ... | DenX | Num10 | Num11 | Num12 | ... | NumX |
| Xyz | 1234 | 4/30/2012 | 3445 | 3 | | | ... | | 2 | 1 | 0 | ... | 0 |
| Xyz | 1234 | 4/30/2012 | 3445 | 3 | | | ... | | 2 | 1 | 0 | ... | 0 |
| Xyz | 1234 | 5/30/2012 | 3456 | 2 | | | ... | | 2 | 2 | 0 | ... | 0 |
| Xyz | 5678 | 6/30/2012 | 9383 | 5 | | | ... | | 4 | 3 | 0 | ... | 0 |
| Xyz | 1234 | 7/2/2012 | 23412 | 7 | | | ... | | 7 | 7 | 0 | ... | 0 |

FIG. 3

| MU_MeasureCore3: Capture Problem List (Patient Age > 2) | | | | | | | | | | | | | |
|---|---|---|---|---|---|---|---|---|---|---|---|---|---|
| ProviderID | PatientID | DOS | EncounterID | Den10 | Den11 | Den12 | ... | DenX | Num10 | Num11 | Num12 | ... | NumX |
| Xyz | 1234 | 4/30/2012 | 3445 | 1 | 1 | 1 | ... | 1 | 1 | 1 | 0 | ... | 0 |
| Xyz | 1234 | 4/30/2012 | 3445 | 1 | 1 | 1 | ... | 1 | 1 | 1 | 0 | ... | 0 |
| Xyz | 1234 | 5/30/2012 | 3456 | 0 | 1 | 0 | ... | 0 | 0 | 0 | 0 | ... | 0 |
| Xyz | 5678 | 6/30/2012 | 9383 | 1 | 1 | 1 | ... | 0 | 1 | 1 | 1 | ... | 0 |
| Xyz | 1234 | 7/2/2012 | 23412 | 1 | 1 | 1 | ... | 1 | 1 | 1 | 0 | ... | 0 |

FIG. 4

| MU_Header | | | | | | | | |
|---|---|---|---|---|---|---|---|---|
| ClientID | ProviderID | PatientID | DOS | EncounterID | RelativeAge | Den1VE | Den2Age2 | Den3Age13 |
| AFM | Xyz | 1234 | 4/30/2012 | 3445 | 2 | 1 | 1 | 0 |
| AFM | Xyz | 1234 | 4/30/2012 | 3445 | 2 | 0 | 1 | 0 |
| AFM | Xyz | 1234 | 5/30/2012 | 3456 | 1 | 0 | 0 | 0 |
| AFM | Xyz | 5678 | 6/30/2012 | 9383 | 14 | 1 | 1 | 1 |
| AFM | Xyz | 1234 | 7/2/2012 | 23412 | 12 | 1 | 1 | 0 |

| | | MU_Details | | | | | | | | | | | | | | | | | | | | | |
|---|---|---|---|---|---|---|---|---|---|---|---|---|---|---|---|---|---|---|---|---|---|---|---|
| | Measure Core 8 | | | | | | | | | | | Measure Core 9 | | | | | | | | | | | |
| | MC8Den1 | MC8Den2 | MC8Den_Final | MC8Num10H | MC8Num11W | MC8Num12S | MC8Num13D | MC8Num_Final | | | | MC9Den1 | MC9Den2 | MC9Den3 | MC9Den4 | MC9Den5 | MC9Den_Final | MC9Num1 | MC9Num2 | MC9Num3 | MC9Num_Final | | |
| | 1 | 0 | 0 | 1234 | 1234 | 0 | 0 | 1 | | | | 1 | 0 | 1 | 1 | 1 | 0 | 1 | | | 0 | | |
| | 1 | 0 | 0 | 1234 | 1234 | 0 | 0 | 1 | | | | 0 | 0 | 1 | 1 | 1 | 0 | 1 | | | 0 | | |
| | 0 | 0 | 0 | 0 | 0 | 0 | 0 | 2 | | | | 0 | 0 | 0 | 1 | 0 | 0 | 0 | | | 0 | | |
| | 1 | 1 | 5678 | 5678 | 5678 | 5678 | 0 | 3 | | | | 1 | 1 | 1 | 1 | 1 | 5678 | 1 | | | 5678 | | |
| | 1 | 0 | 0 | 1234 | 1234 | 1234 | 1234 | 7 | | | | 1 | 0 | 1 | 1 | 1 | 0 | 1 | | | 0 | | |

Count(Distinct MC8Den_Final)
Count(Distinct MC9Den_Final)
Count(Distinct MC9Num_Final)

MC8NumH = Count(Distinct MC8Num10H)
MC8NumW = Count(Distinct MC8Num11W)
MC8NumS = Count(Distinct MC8Num12S)
MC8NumD = Count(Distinct MC8Num13D)
MC8Num_Final = MC8NumH$^0$ * MC8NumW$^0$ * MC8NumS$^0$ * MC8NumD$^0$ * PatientID ☐ = numerator of Measure Core N
■ = denominator of Measure Core N

*FIG. 6B*

```
SELECT    COUNT(DISTINCT(Core5_Numerator)),    -returns a distinct # of patients
          COUNT(DISTINCT(Core5_Denominator))
FROM      FunMeasMU2.MU_Details
```

*FIG. 7*

```
EXEC report.spdm_MU_getAllPatientEncounters
    @pSessionID = '625436',
    @pProviderID = 62,
    @p_ClientID = 1,
    @pHeaderOrDetails = 'd',
    @pReportingStartDate = '01/01/2000',
    @pReportingEndDate = '12/31/2015',
    @pReportAsOfDate = NULL,
    @pMeasure = 'core3'
```

| # | providerid | servicedate | MRN | firstname | lastname | m | dobdttm | g | Core3_Num_isLanguageCaptured | Core3_Num_isSexCaptured |
|---|---|---|---|---|---|---|---|---|---|---|
| 1 | 70517 | 2005-02-10 08:06:00.000 | 113475500 | TIKKUS | SETTLKIT | J | 1945-01-11 | M | NULL | NULL |
| 2 | 150 | 2005-01-25 15:02:00.000 | 113475500 | REOEYT | MARTIOER | P | 1936-10-26 | F | NULL | NULL |
| 3 | 157 | 2005-02-15 17:49:00.000 | 113475500 | ELMMIK | GUTIEMLE | | 1932-09-06 | F | NULL | NULL |
| 4 | 150 | 2007-02-23 13:04:00.000 | 113475500 | REOEYT | MARTIOER | P | 1936-10-26 | F | NULL | NULL |
| 5 | 151 | 2007-12-06 11:57:00.000 | 113475500 | XEBMEI | HEBERBEX | H | 1947-03-25 | M | NULL | NULL |
| 6 | 112 | 2008-02-22 09:00:00.000 | 113475500 | YAGCAJ | SHRAGGAY | L | 1972-12-26 | F | NULL | 1 |
| 7 | 154 | 2008-09-19 11:35:00.000 | 113475500 | TYESHA | WARREEYT | B | 1948-05-12 | F | NULL | NULL |
| 8 | 151 | 2007-06-21 11:54:00.000 | 113475500 | JOEROT | FIFEEOJ | | 1948-11-15 | F | NULL | NULL |
| 9 | 152 | 2008-08-29 12:05:00.000 | 113475500 | VEJMAX | HYDEJEV | A | 1945-10-27 | F | NULL | NULL |
| 10 | 112 | 2007-02-21 14:06:00.000 | 113475500 | YADIRE | FIFFDAY | R | 1956-04-20 | M | NULL | NULL |

Query executed successfully.   |SANDBAR (11.0 SP1) |CORPORATE\gblackwell (81)|CDW_REP| 00:00:04 | 61753 rows

*FIG. 8*

RAPID REPORTING OF MEANINGFUL USE IN ELECTRONIC HEALTH RECORDS

CROSS-REFERENCE TO RELATED APPLICATION

The present application is a U.S. nonprovisional patent application of, and claims priority under 35 U.S.C. § 119(e) to, U.S. provisional patent application Ser. No. 61/868,516, filed Aug. 21, 2013, which provisional patent application is incorporated herein by reference.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention generally relates to rapid reporting of meaningful use of electronic health records and related technology within a healthcare organization.

Meaningful use (MU), in a health information technology (HIT) context, refers to the use of electronic health records (EHR) and related technology within a healthcare organization in a way that meets certain criteria. It has been said that meaningful use means "providers need to show they're using certified EHR technology in ways that can be measured significantly in quality and in quantity." In the U.S., achieving meaningful use can be a requirement for receiving federal funding under some incentive programs.

Implementation of the Meaningful Use system in the U.S. has been divided into three stages, with the first (stage 1) being used as an eligibility criteria beginning in the 2011-2012 timeframe and the others being used in years thereafter. Stage 1 sets the basic functionalities for EHRs. More particularly, Stage 1 meaningful use criteria set the baseline for electronic data capture and information sharing. The requirements are focused on providers capturing patient data and sharing that data either with the patient or with other healthcare professionals. In at least some programs, eligible professionals, eligible hospitals, and critical access hospitals will successfully attest to two stage 1 reporting periods before moving to stage 2.

The first steps in achieving meaningful use are to have a certified electronic health record (EHR) and to be able to demonstrate that it is being used to meet the requirements. Stage 1 contains 25 objectives/measures for Eligible Providers (EPs) and 24 objectives/measures for eligible hospitals (EHs). The objectives/measures have been divided into a core set and a menu set. EPs and EHs must meet all objectives/measures in the core set (15 for EPs and 14 for EHs). EPs must meet 5 of the 10 menu-set items during Stage 1, one of which must be a public health objective. The core requirements for Stage 1 include: (1) use computerized order entry for medication orders; (2) implement drug-drug, drug-allergy checks; (3) generate and transmit permissible prescriptions electronically; (4) record demographics; (5) maintain an up-to-date problem list of current and active diagnoses; (6) maintain active medication list; (7) maintain active medication allergy list; (8) record and chart changes in vital signs; (9) record smoking status for patients 13 years old or older; (10) implement one clinical decision support rule; (11) report ambulatory quality measures to Center for Medicare & Medicaid Services (CMS) or the States; (12) provider patients with an electronic copy of their health information upon request; (13) provide clinical summaries to patients for each office visit; (14) capability to exchange key clinical information electronically among providers and patient-authorized entities; and (15) protect electronic health information (privacy and security). A list of the menu requirements is not set forth herein but is readily available from a wide variety of sources.

Compliance with the requirements entails the creation of many reports based on all of an EP's or EH's patient encounters. Prior art meaningful use (stage 1) systems complete all the computational processing for a particular report at the time the report is created. Unfortunately, when used on a large scale, prior art approaches perform numerous and repeated aggregations and conditions against millions or billions of records to calculate Meaningful Use (stage 1) reports. Furthermore, as client demand for reports increases, the probability of dead-locking increases exponentially, forcing report requests to be placed in a queue for processing. This queuing effect can delay report production for hours (often to the next day) and has become a substantial source of dissatisfaction for users. Users are often so dissatisfied that they use various tools to automatically trigger report generation at a predetermined interval, regardless of whether a report is actually needed. This in turn compounds the problem by escalating the demand on servers which leads to slower performance.

A secondary issue relates to the demand placed on the hardware in terms of processing and disk demands. Driven by an enormous amount of data I/O, the uninterrupted load tends to decrease the life of system hardware. Not only does this directly increase infrastructure cost, but it increases the potential for downtime as well as the loss of data.

It is believed that an improved framework could be architected and implemented that would deliver accurate and timely results in seconds rather than hours, thereby improving the value and insights of Meaningful Use. One or more aspects and features of the invention are believed to provide such enhancement.

SUMMARY OF THE INVENTION

The present invention includes many aspects and features. Moreover, while many aspects and features relate to, and are described in, the context of rapid reporting of meaningful use of electronic health records, the present invention is not limited to use only in rapid reporting of meaningful use of electronic health records, as will become apparent from the following summaries and detailed descriptions of aspects, features, and one or more embodiments of the present invention.

Accordingly, one aspect of the present invention relates to a system comprising a non-transitory computer-readable medium containing computer-executable instructions for providing a method related to rapid reporting of meaningful use in electronic health records. An exemplary such method includes storing patient encounter data in a database; pre-calculating data related to at least one meaningful use measure; storing the pre-calculated data in a plurality of small staging tables; and compiling the pre-calculated and stored data from the small staging tables into a single table that is adapted to be accessed by reporting software.

In a variation of this aspect, the storing step includes storing unique identifiers, rather than standard Boolean values, as flags and/or indicators.

In features of this aspect of the invention, the storing step includes storing unique patient identifiers as flags and/or indicators; the storing step includes storing unique encounter identifiers as flags and/or indicators; and/or the method further includes a step of using a common aggregate function to solve for a final meaningful use data score. With regard to the latter feature, in further features, the common aggregate function is a COUNT function; the common aggregate function is a SUM function; the step of using a common aggregate function to solve for a final meaningful use data score includes determining a numerator by carrying out a first common aggregate function, and determining a denominator by carrying out a second common aggregate function; and/or the step of using a common aggregate function is carried out given a dynamic time period.

In another variation of this aspect, the step of pre-calculating data related to at least one meaningful use measure is carried out without respect to a known timeframe.

In another variation of this aspect, the step of storing the pre-calculated data in a plurality of small staging tables includes storing the pre-calculated data with a common grain to allow for easy retrieval of results.

In another variation of this aspect, the step of storing the pre-calculated data is carried out independent of the time period.

In another variation of this aspect, the method further includes the step of accessing the single table via reporting software.

Another aspect of the invention relates to a method related to rapid reporting of meaningful use in electronic health records. An exemplary such method includes: storing patient encounter data in a database; pre-calculating data related to at least one meaningful use measure; storing the pre-calculated data in a plurality of small staging tables; and compiling the pre-calculated and stored data from the small staging tables into a single table that is adapted to be accessed by reporting software.

In a variation of this aspect, the storing step includes storing unique identifiers, rather than standard Boolean values, as flags and/or indicators.

Another aspect of the invention relates to a system comprising a method related to rapid reporting of meaningful use in electronic health records. An exemplary such method includes: storing patient encounter data in a database; pre-calculating data related to at least one meaningful use measure; storing the pre-calculated data in a plurality of small staging tables; and compiling the pre-calculated and stored data from the small staging tables into a single table that is adapted to be accessed by reporting software.

In a variation of this aspect, the storing step includes storing unique identifiers, rather than standard Boolean values, as flags and/or indicators.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings, wherein the same elements are referred to with the same reference numerals, and wherein.

DETAILED DESCRIPTION

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. § 112, 16, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the present invention are next described. The following description of one or more preferred embodiments is merely exemplary in nature and is in no way intended to limit the invention, its implementations, or uses. Specific details and features thereof are found in the incorporated materials accompanying the specification of the present application.

Meaningful Use metrics are typically of the form of counting unique items like patients or encounters and have the added complexity of only needing to be captured once in a given period of time, such as 90 days (or a calendar quarter). Knowing that Meaningful Use Stage 1 metrics can be calculated on any 90 day continuous period within an attestation year, a structure is created to store the data with a common grain to allow for easy retrieval of the results. In the present invention, an initial step is the effective pre-calculation of results with respect to a known time frame. In at least one contemplated commercial embodiment, the system leverages processes to extract, translate, and load (ETL) aggregated information in a unique and novel manner that enables extraordinarily rapid response times. The data drawn from raw encounter data is translated and stored in a series of small staging tables that contain discrete results related to each meaningful use measure. Once all measures are completed, a secondary process compiles the smaller tables into a single table (MU_Details) that would be directly accessed by the reporting software.

FIGS. 1-5 are graphical illustrations of a plurality of small staging tables in which data has been pre-calculated and stored for subsequent compilation into a single large table.

Figure 1:
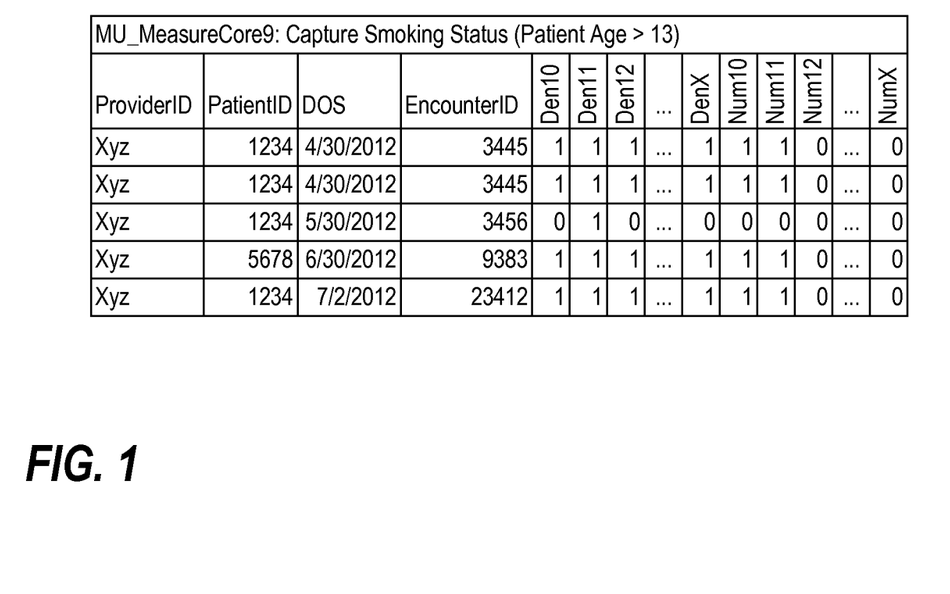
FIGS. 1-5 are graphical illustrations of a plurality of small staging tables in which data has been pre-calculated and stored for subsequent compilation into a single large table, all in accordance with one or more preferred embodiments of the present invention.
Figure 2:
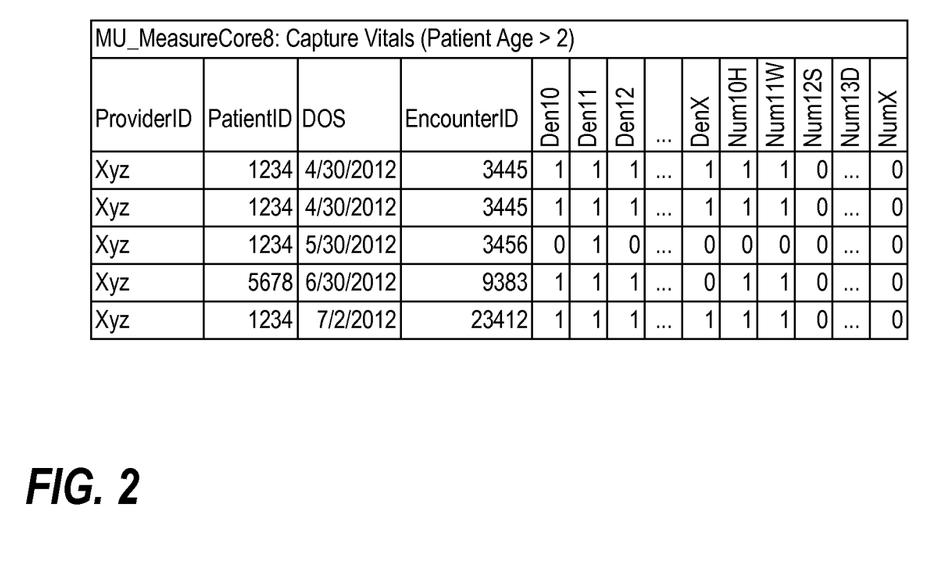
Figure 3:
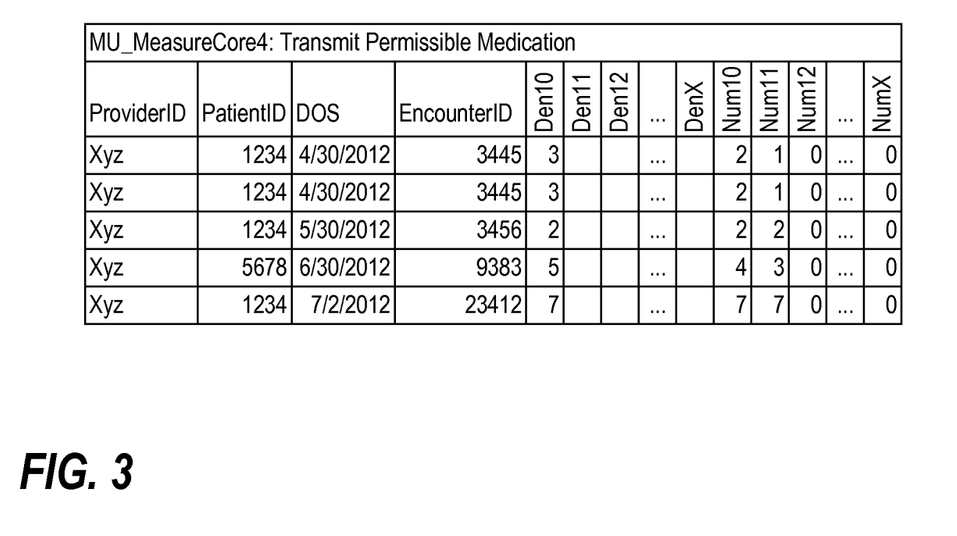
Figure 4:
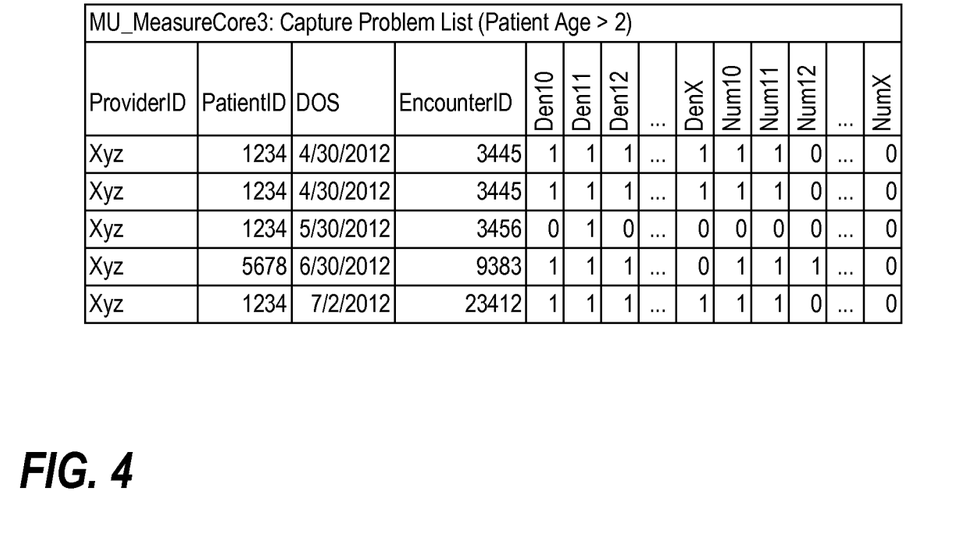
Figure 5:
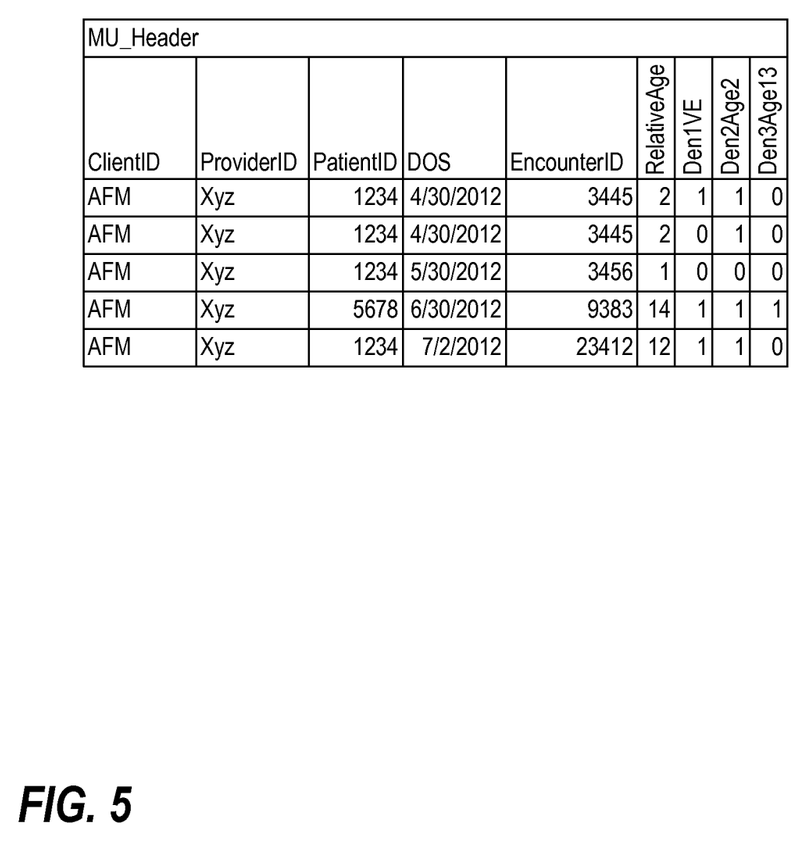

In particular, FIG. 1 illustrates a table (MU_MeasureCore9) that pertains to core Measure 9 of Meaningful Use Stage 1 (Measure 5 of Meaningful Use Stage 2), FIG. 2 illustrates a table (MU_MeasureCore8) that pertains to core Measure 8 (where H=height, W=weight, S=systolic blood pressure, and D=diastolic blood pressure), FIG. 3 illustrates a table (MU_MeasureCore4) that pertains to core Measure 4, and FIG. 4 illustrates a table (MU_MeasureCore3) that pertains to core Measure 3. In each case, patient encounter data pertaining to the respective measure is pre-calculated and stored in association with key data like provider identifier (ProviderID), patient identifier (PatientID), DOS, and encounter identifier (EncounterID). In particular, Boolean values pertaining to the patient encounter are stored for both the numerator and the denominator. The key data is also stored in the table (MU_Header) in FIG. 5, which also includes common dimension data, like client identifier (ClientID) and relative patient age, and common premeasure data.

Figure 6A:
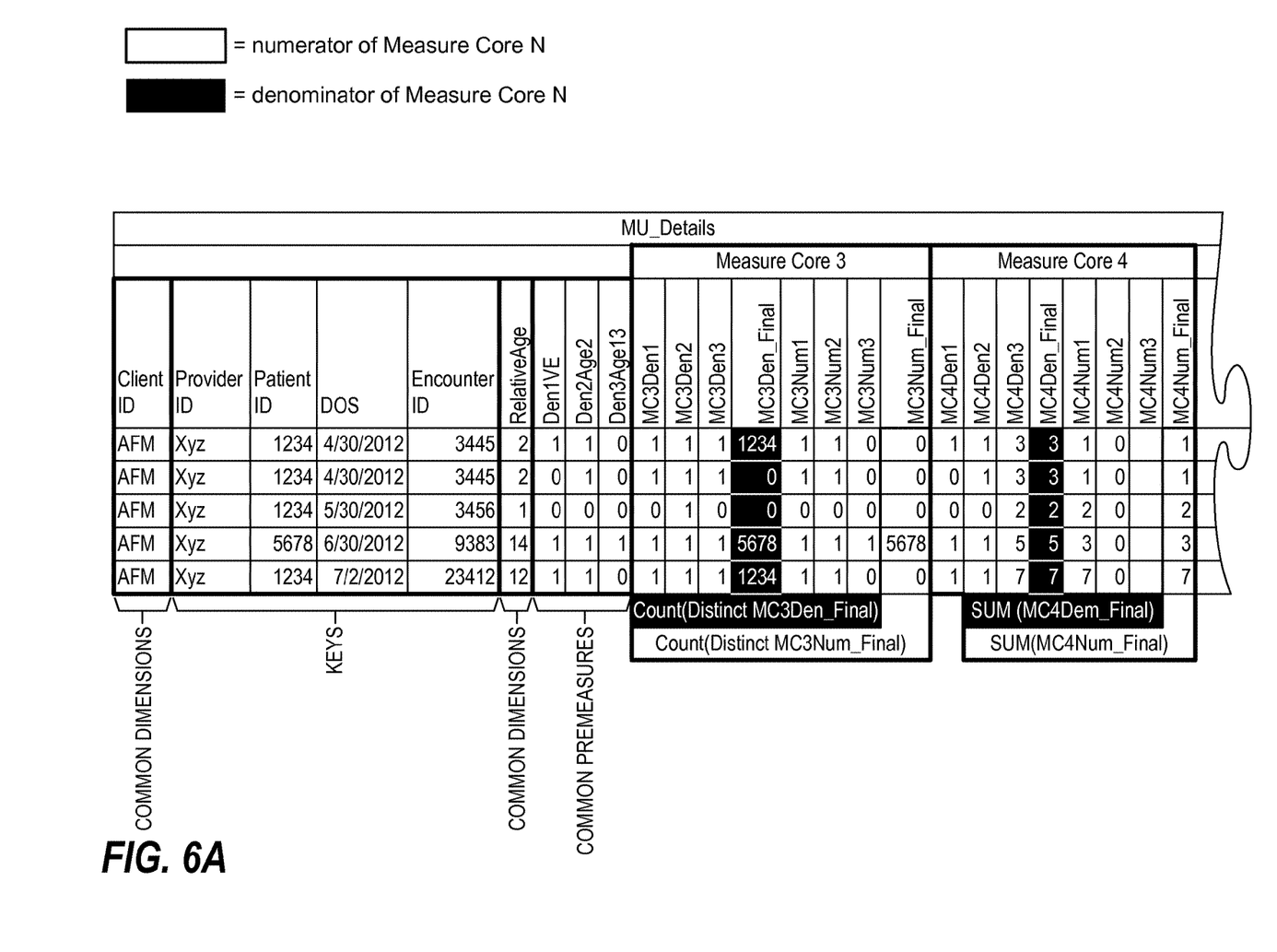
FIGS. 6A and 6B are a graphical illustration of a single large table containing a compilation of the data in FIGS. 1-5.
Figure 6B:
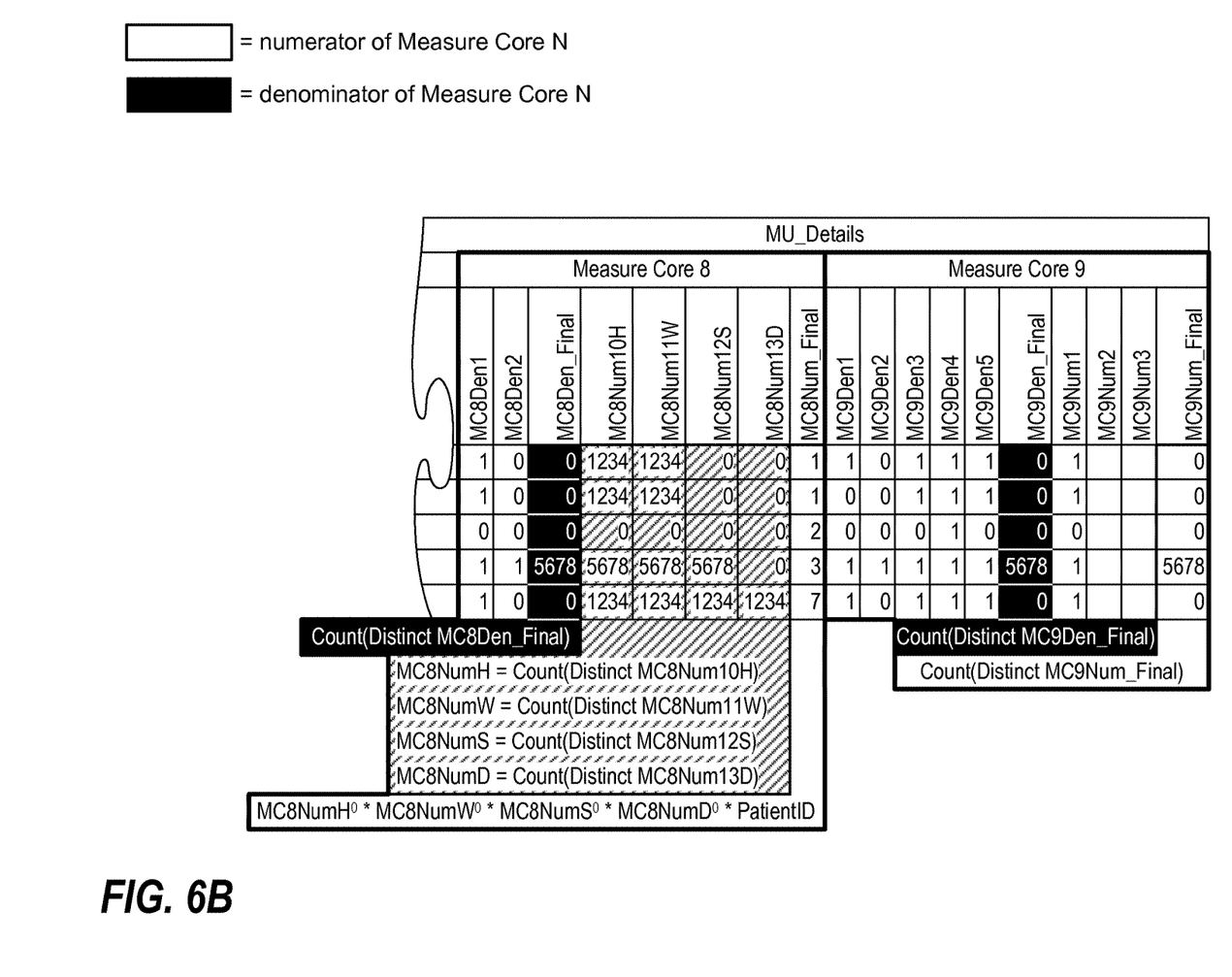

The data from the staging tables in FIGS. 1-5 is then compiled into a single table. In this regard, FIGS. 6A and 6B are a graphical illustration of a single large table containing a compilation of the data in FIGS. 1-5. As shown therein, the table of FIGS. 6A and 6B, which is organized by encounter identifier and includes other key data, common dimension data, and premeasure data from the MU_Header table of FIG. 5, also includes data from the various tables (MU_MeasureCore9, MU_MeasureCore8, MU_MeasureCore4, and MU_MeasureCore3) of FIGS. 1-4.

At least one inventive step within the framework of the present invention regards how data is systematically stored. In at least one contemplated commercial embodiment, core functionality of Microsoft SQL (MS SQL) is leveraged to optimize performance. In particular, unique IDs (e.g., patient identifiers, encounter identifiers, or the like) are stored as flags or indicators for each Meaningful Use measure rather storing the standard Boolean values of True and False. This approach allows the database to leverage common aggregation functions, such as:

COUNT(DISTINCT( . . . ))

and

SUM( . . . )

to easily count distinct values and other solve for final scores given a dynamic time period. Leveraging this pattern, it is possible to express the meaningful use measure as a pre-calculation that is independent of time.

For example, Measure 9 of Meaningful Use Stage 1 (Measure 5 of Meaningful Use Stage 2) requires a provider to express the number of patients over the age of 13 where the provider captured their smoking status. The result must be represented as a ratio of the number of patients whose smoking status was captured to the total number of patients, but excluding all patients that are 13 or younger from the calculations. In other words, the numerator of the ratio is the number of patients, over age 13, whose smoking status was captured, while the denominator of the ratio is the total number of patients that were over age 13 at the time the particular patient encounter occurred.

This may be accomplished as follows. The relevant patient encounter data is stored in the staging table (MU_MeasureCore9) of FIG. 1 and then compiled into the large table (MU_Details) of FIGS. 6A and 6B. The patient identifier, rather than a Boolean value (true or false) is stored in the numerator field for encounters where the smoking status was captured and the patient was of the proper age; otherwise, the field remains null (no value). Similarly, the patient identifier is stored in the denominator field if the patient is of age, regardless of whether the smoking status was captured.

The measure itself may then be calculated extremely rapidly by merely aggregating a count of distinct patient identifiers, i.e.:

Measure 9=Count(Distinct $MC9Num\_Final$)/Count (Distinct $MC9Den\_Final$)

Other measures in FIGS. 6A and 6B are calculated using the numerators and denominators shown therein.

Figure 7:
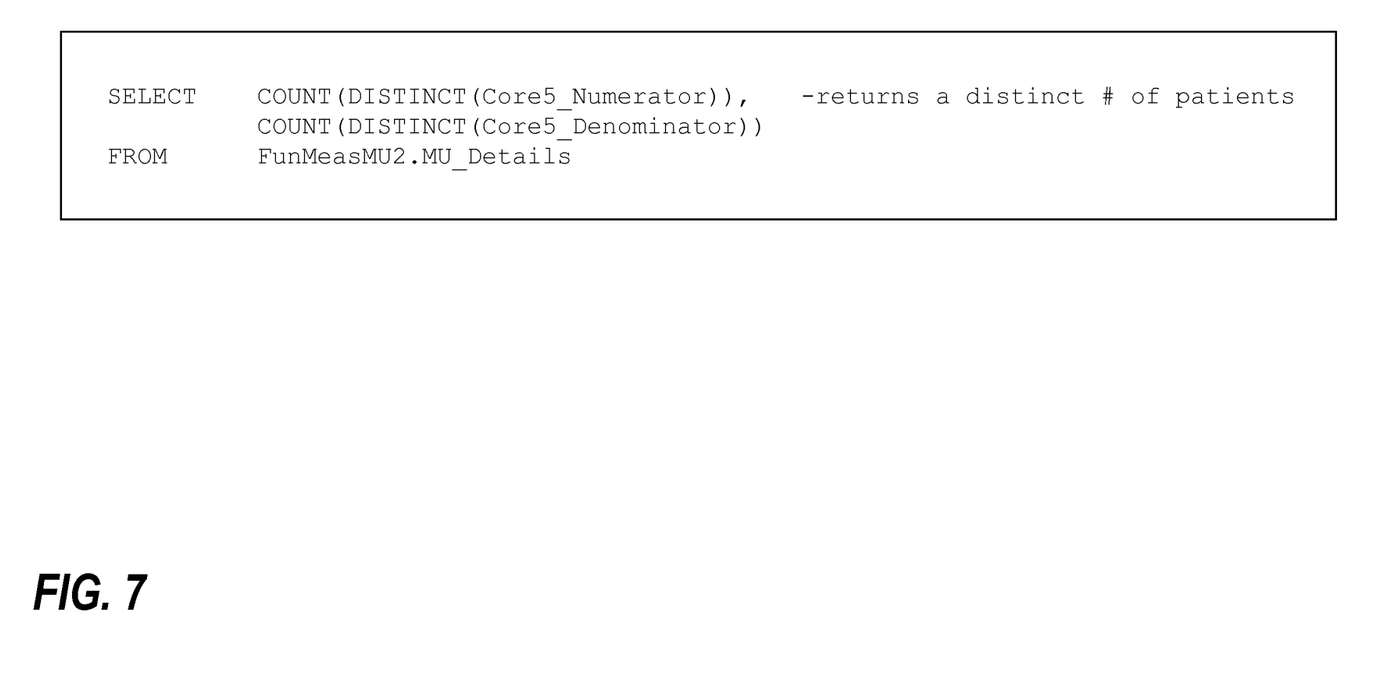
FIG. 7 is a generalized example of pseudo code used to accomplish at least one step of methods in accordance with one or more aspects of the present invention.

FIG. 7 is a generalized example of pseudo code used to accomplish the foregoing. However, while the example generalizes the approach for high-level understanding, the actual code may differ significantly as it must consider multiple elaborate steps to capture the various facets that surround regulations dictated by the Center for Medicare & Medicaid Services (CMS).

Figure 8:
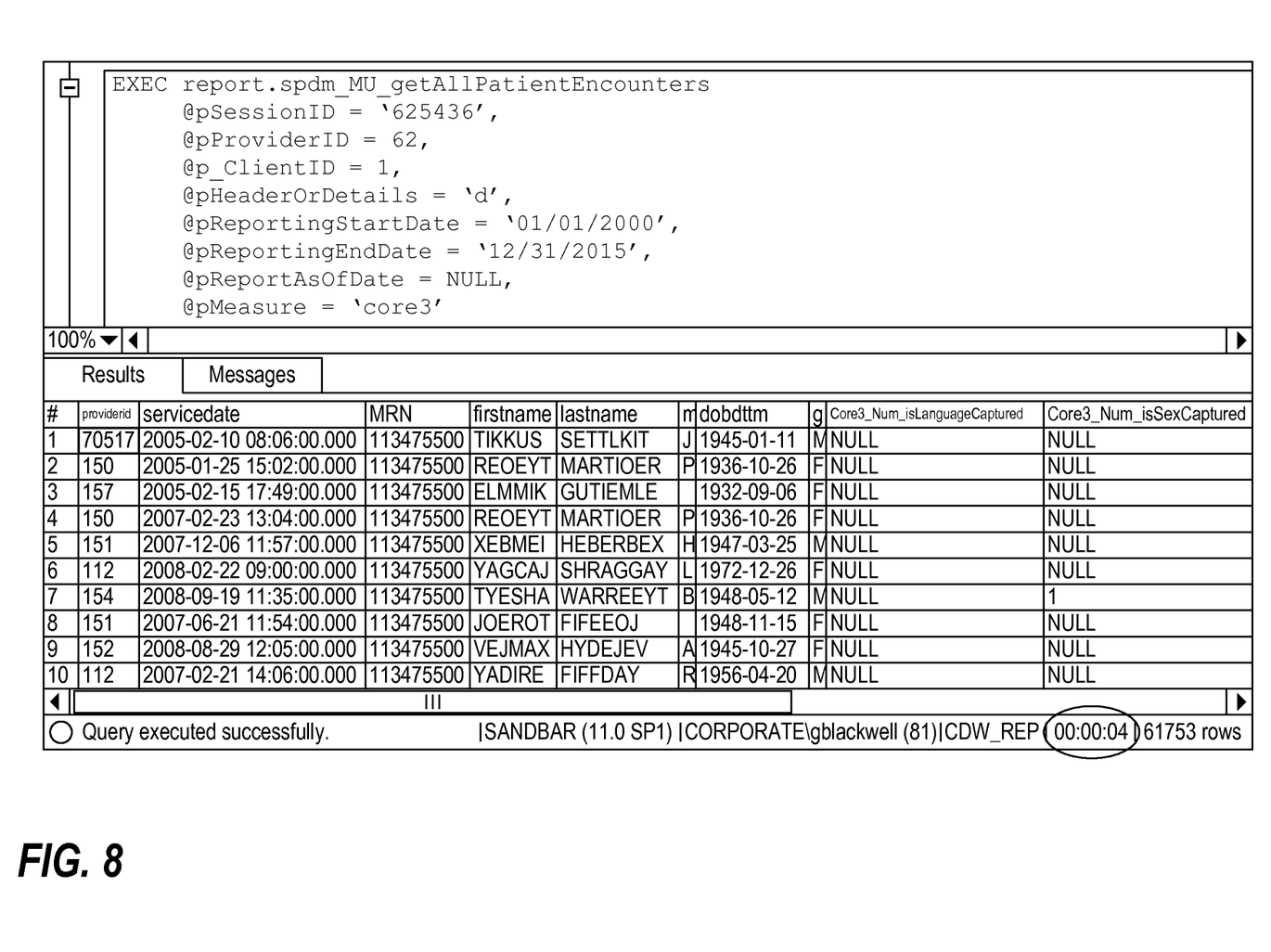
FIG. 8 is a portion of an exemplary screenshot illustrating results recorded during a demonstration of an embodiment of a framework developed in accordance with one or more aspects of the present invention.

Using the present invention, the time taken for regeneration of reports has been reduced from hours to seconds. FIG. 8 is a portion of an exemplary screenshot illustrating results recorded during a demonstration of an embodiment of a framework developed in accordance with one or more aspects of the present invention. As shown therein, the reports were generated in only 4 seconds (00:00:04).

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention.

Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A processor-based method of optimizing the generation of electronic reports of meaningful use in an electronic health records (EHR) computer system, comprising:
    receiving patient encounter data in a database, wherein the patient encounter data comprises Boolean values;
    pre-calculating first data related to a first meaningful use measure associated with at least a portion of the patient encounter data;
    storing the pre-calculated first data in a first small staging table;
    pre-calculating second data related to a second meaningful use measure associated with at least a portion of the patient encounter data;
    storing the pre-calculated second data in a second small staging table;
    processing the pre-calculated first data of the first small staging table to generate a first data column representing the first meaningful use measure without Boolean values, wherein a value of true is represented by a unique patient identifier, and a value of false is represented by a null value;
    compiling the processed first small staging table and second small staging table into a single table;
    accessing the single table via reporting software to calculate a meaningful use metric related to the first data column of the first meaningful use measure, the calculation comprising determining a number of unique values contained in the first data column; and
    generating an electronic report for the EHR computer system comprising the meaningful use metric.

2. The system of claim 1, wherein calculating the meaningful use metric comprises using a common aggregate function to solve for a final meaningful use data score.

3. The system of claim 2, wherein the common aggregate function is a COUNT function.

4. The system of claim 2, wherein the common aggregate function is a SUM function.

5. The system of claim 2, wherein using a common aggregate function to solve for a final meaningful use data score includes determining a numerator by carrying out a first common aggregate function, and determining a denominator by carrying out a second common aggregate function.

6. The system of claim 2, wherein using a common aggregate function is carried out given a dynamic time period.

7. The system of claim 2, wherein the step of pre-calculating data related to a first meaningful use measure is carried out without respect to a known timeframe.

8. The system of claim 2, wherein the storing the pre-calculated data in first and second small staging tables comprises storing the pre-calculated data with a common grain to optimize retrieval of results.

9. The system of claim 2, wherein the step of storing the pre-calculated data is carried out independent of the time period.

10. The system of claim 2, further comprising the step of accessing the single table via reporting software.

* * * * *